United States Patent
Parodi

(10) Patent No.: US 7,591,842 B2
(45) Date of Patent: Sep. 22, 2009

(54) ENDOVASCULAR PROSTHESIS WITH SUTURE HOLDER

(75) Inventor: Juan C. Parodi, Buenos Aires (AR)

(73) Assignee: Aptus Endosystems, Inc., Sunnyvale, CA (US)

( * ) Notice: Subject to any disclaimer, the term of this patent is extended or adjusted under 35 U.S.C. 154(b) by 704 days.

(21) Appl. No.: 09/935,893

(22) Filed: Aug. 23, 2001

(65) Prior Publication Data

US 2003/0093146 A1 May 15, 2003

Related U.S. Application Data

(63) Continuation of application No. 09/640,819, filed on Aug. 17, 2000, now abandoned, which is a continuation of application No. 09/266,136, filed on Mar. 10, 1999, now abandoned.

(51) Int. Cl.
A61F 2/06 (2006.01)
A61M 29/00 (2006.01)

(52) U.S. Cl. ...................... 623/1.11; 606/108

(58) Field of Classification Search ............... 623/1.1, 623/1.4, 1.12, 1.13, 1.14, 1.15, 1.16, 1.17, 623/1.18, 1.19, 1.2, 1.32, 1.36, 1.11; 656/108, 656/191, 194, 195, 190; 606/185, 186, 213, 606/219–220, 192, 194, 195, 108

See application file for complete search history.

(56) References Cited

U.S. PATENT DOCUMENTS

| | | | |
|---|---|---|---|
| 2,033,039 A | 3/1936 | Limpert | |
| 3,686,740 A | 8/1972 | Shiley | |
| 3,799,172 A | 3/1974 | Szpur | |
| 4,140,126 A | 2/1979 | Choudhury | |
| 4,307,722 A | 12/1981 | Evans | |
| 4,580,568 A | 4/1986 | Gianturco | |
| 4,781,682 A | 11/1988 | Patel | |
| 4,898,577 A | 2/1990 | Badger et al. | |
| 4,921,484 A | 5/1990 | Hillstead | |

(Continued)

FOREIGN PATENT DOCUMENTS

| | | |
|---|---|---|
| EP | 0321912 A1 | 12/1987 |
| EP | 0663184 A1 | 1/1994 |
| FR | 2 299 548 | 1/1975 |
| WO | WO 97/03616 | 2/1997 |
| WO | WO 99/53845 | 10/1999 |

OTHER PUBLICATIONS

Advertising literature entitled "5mm Origin Tacker™ It Runs in Circles Around Staples" (origin) copyright 1995, with attached article entitled "The S piral Tacker: A New Technique for Stabilizing Prosthetic Mesh in Laparoscopic Hernia Repair" Nov. 1995, *Surgical Rounds*.
MedPro Month Oct. 1995, "Laparoscopic Surgery".
Newman III, et al. Assisted TAPP Procedure Circa 1995.
Hatchet, Lawrence, et al. "Extraperitoneal Endoscopic Burch Repair Using a Tacker Mesh Technique", Circa 1995.

*Primary Examiner*—Vy Q. Bui
(74) *Attorney, Agent, or Firm*—Ryan Kromholz & Manion S.C.

(57) ABSTRACT

An endovascular prosthesis has a prosthesis body that is sized and configured for introduction into a blood vessel lumen. The prosthesis body has a wall that defines an interior passage for blood. One or more connectors are distributed about the wall. A fastener is carried by at least one of the connectors. The fastener is sized and configured for advancement through the connector into tissue in the blood vessel lumen.

3 Claims, 2 Drawing Sheets

U.S. PATENT DOCUMENTS

| | | | | |
|---|---|---|---|---|
| 5,030,204 A | | 7/1991 | Badger et al. | |
| 5,042,707 A | | 8/1991 | Taheri | |
| 5,071,407 A | | 12/1991 | Termin et al. | |
| 5,104,399 A | | 4/1992 | Lazarus | |
| 5,330,490 A | | 7/1994 | Wilk et al. | |
| 5,330,503 A | * | 7/1994 | Yoon | 606/223 |
| 5,470,337 A | | 11/1995 | Moss | |
| 5,480,382 A | | 1/1996 | Hammerslag et al. | |
| 5,489,295 A | | 2/1996 | Piplani et al. | |
| 5,562,728 A | | 10/1996 | Lazarus et al. | |
| 5,571,171 A | | 11/1996 | Barone et al. | |
| 5,571,173 A | | 11/1996 | Parodi | |
| 5,582,616 A | | 12/1996 | Bolduc et al. | |
| 5,662,700 A | | 9/1997 | Lazarus | |
| 5,676,696 A | | 10/1997 | Marcade | |
| 5,676,697 A | | 10/1997 | McDonald | |
| 5,700,269 A | | 12/1997 | Pinchuk et al. | |
| 5,702,365 A | | 12/1997 | King | |
| 5,713,907 A | | 2/1998 | Hogendijk et al. | |
| 5,810,882 A | | 9/1998 | Bolduc et al. | |
| 5,824,008 A | | 10/1998 | Bolduc et al. | |
| 5,824,041 A | | 10/1998 | Lenker et al. | |
| 5,855,565 A | | 1/1999 | Bar-Cohen et al. | |
| 5,957,940 A | * | 9/1999 | Tanner et al. | 606/155 |
| 5,964,772 A | | 10/1999 | Bolduc et al. | |
| 5,968,053 A | | 10/1999 | Revelas | |
| 5,972,023 A | | 10/1999 | Tanner et al. | |
| 5,980,548 A | * | 11/1999 | Evans et al. | 606/185 |
| 5,993,401 A | | 11/1999 | Inbe et al. | |
| 5,993,466 A | | 11/1999 | Yoon | |
| 6,074,418 A | * | 6/2000 | Buchanan et al. | 623/2.11 |
| 6,126,685 A | | 10/2000 | Lenker et al. | |
| 6,145,509 A | | 11/2000 | Tanner | |
| 6,217,597 B1 | | 4/2001 | Tanner | |
| 6,248,118 B1 | | 6/2001 | Tanner et al. | |
| 6,258,119 B1 | | 7/2001 | Hussein et al. | |
| 6,270,516 B1 | | 8/2001 | Tanner et al. | |
| 6,287,315 B1 | | 9/2001 | Wijeratne et al. | |
| 6,296,656 B1 | | 10/2001 | Bolduc et al. | |
| 6,302,906 B1 | | 10/2001 | Goicoechea et al. | |
| 6,336,933 B1 | | 1/2002 | Parodi | |
| 6,371,919 B1 | | 4/2002 | Tanner et al. | |
| 6,409,757 B1 | | 6/2002 | Trout, III et al. | |
| 6,428,565 B1 | | 8/2002 | Wisselink | |
| 6,520,974 B2 | | 2/2003 | Tanner et al. | |
| 6,544,253 B1 | | 4/2003 | Tanner | |
| 6,562,051 B1 | | 5/2003 | Bolduc et al. | |
| 6,592,593 B1 | | 7/2003 | Parodi et al. | |

* cited by examiner

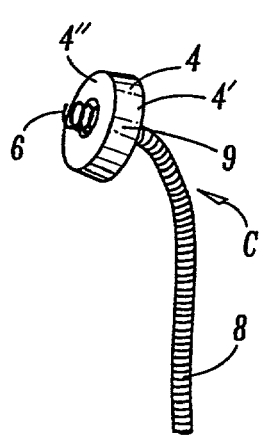
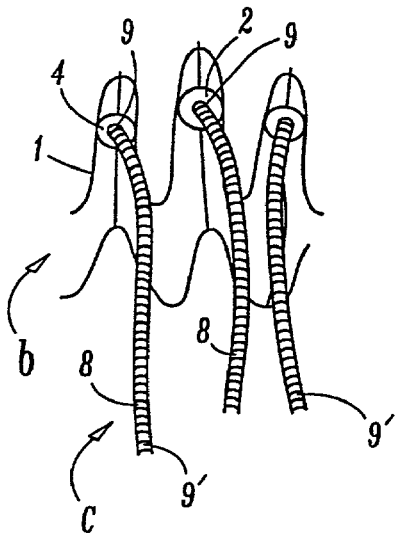
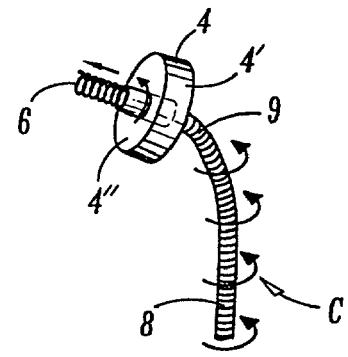
FIG. 2a  FIG. 1  FIG. 2b
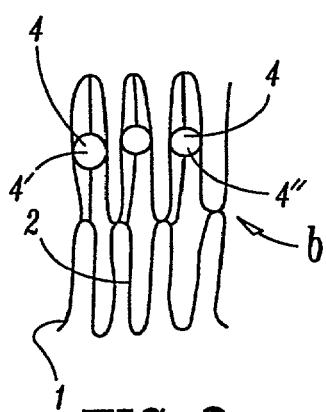
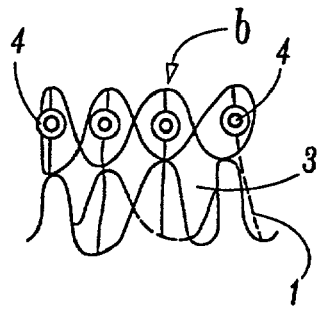
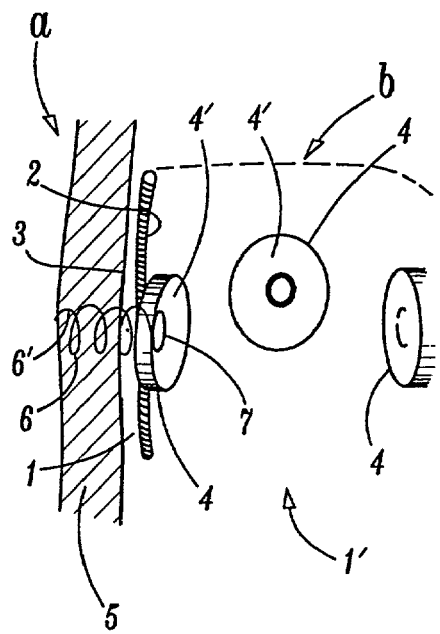
FIG. 3  FIG. 4  FIG. 4a

ENDOVASCULAR PROSTHESIS WITH SUTURE HOLDER

RELATED APPLICATIONS

This application is a continuation of U.S. patent application Ser. No. 09/640,819, filed Aug. 17, 2000 (Abandoned), which is a continuation of U.S. patent application Ser. No. 09/266,136, filed Mar. 10, 1999 (Abandoned), which claims foreign priority benefits under 35 U.S.C. § 119 of Argentina Application No. P19980101144, filed Mar. 13, 1998.

FIELD OF THE INVENTION

This invention consists of an endovascular device with suture holder that permits creation of a firm union between the prosthesis and the vascular walls with no need to introduce suture applicator devices into the vascular channel.

BACKGROUND OF THE INVENTION

To treated diseases of the arterial and venous channels, recourse is had to endovascular treatments based on the application of expandable prostheses or endoluminal expanders that permit the affected vascular walls to be covered and thus provide an effective solution to problems that would otherwise cause a high rate of mortality.

Nonetheless, the new application techniques and devices must solve problems such as how to avoid vascular dilation subsequent to the treatment causing periprosthetic losses resulting in consequences difficult to solve.

To avoid this type of problem, internal sutures are used that prove highly effective in obtaining a firm union between the vascular walls and the body of the prosthesis.

These endovascular sutures consist of metal spirals provided with an sharp penetrating end and an anchoring end that are applied by means of devices equipped with rotary applicator heads. In this manner, the above-mentioned spirals pass through the walls of the prosthesis first, and then the vascular walls, achieving a very firm union by means of which the sutured prosthesis conveniently accompanies the dilation of the vascular channel.

However, the known devices used for this type of treatment include a set of means such as distal or proximal inflatable balloons, tubular parts that provide a surgical method in which a rotary pusher for the above-cited spiral sutures, auxiliary lines, etc., can function.

In addition, these devices have a function based on the fact that the operations for introducing the sutures are performed inside the vascular channel.

SUMMARY OF THE INVENTION

This device permits disposing of devices such as those mentioned, since both the sutures and the means of application are mounted on the prosthesis itself.

Basically it comprises a prosthetic body over the internal surfaces of which a number of connectors are distributed and attached; on the one hand, they connect the respective semi-flexible cables to external, rotary control ends while, on the other hand, they are passed through by respective spiral sutures controlled by said semi-flexible cables.

That is, the spiral sutures are already applied to the prosthetic body, as are the semi-flexible applicator cables. Once the prosthetic body is expanded, its external surfaces are backed against the vascular walls. With this arrangement, the rotary actuation of the semi-flexible cables permit the penetrating ends of the spirals to pass though the vascular walls. This penetration continues until the anchoring tips of the above-cited spirals meets the bases of their respective connectors. In this manner, a firm union is created between the vascular channel and the prosthetic body and the semi-flexible cables are simply disconnected and withdrawn.

This creates an endovascular prosthesis that does not require the introduction of additional applicators, that simplifies placement operations and is more economical than other devices currently in use.

BRIEF DESCRIPTION OF THE DRAWINGS

For greater clarity and better comprehension of the subject of the invention, it is illustrated within various figures showing one of the preferred methods of embodiment, all as a simple illustrative and not limitative example.

FIG. 1 is a perspective view of the interior passage of the prosthetic body showing the semi-flexible cables and corresponding connectors.

FIG. 2a is a perspective view of a connector with its respective semi-flexible cable. A spiral suture appears through the mouth of the connector.

FIG. 2b is a perspective view, as in FIG. 2a, but showing how the rotation of the cable causes the spiral to advance.

FIG. 3 is a perspective view of the internal surface of the prosthetic body.

FIG. 4 is a perspective view of the external surface of the prosthetic body.

FIG. 4a is a longitudinal cross-section of the prosthetic body and the vascular channel for the application once the spiral sutures have been applied and the respective semi-flexible cables disconnected.

In the various Figures, the same reference numbers indicate the same or similar parts, and the sets of various components are indicated by letters.

Figure 5A:
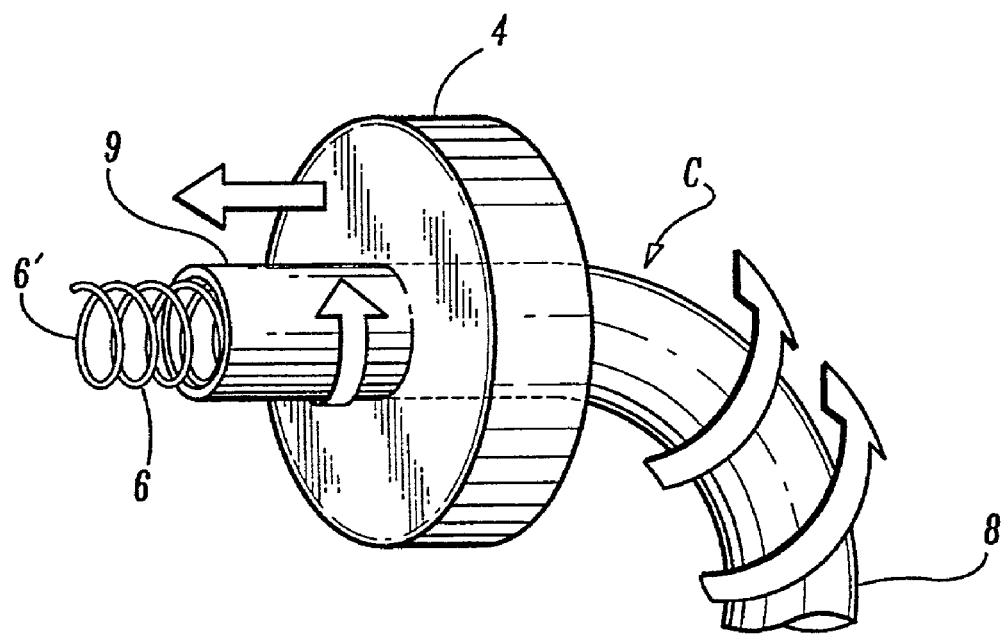
FIG. 5a is a perspective detail of a connector and the applicator end of the semi-flexible cable in which the application movements of the spiral suture are shown.
Figure 5B:
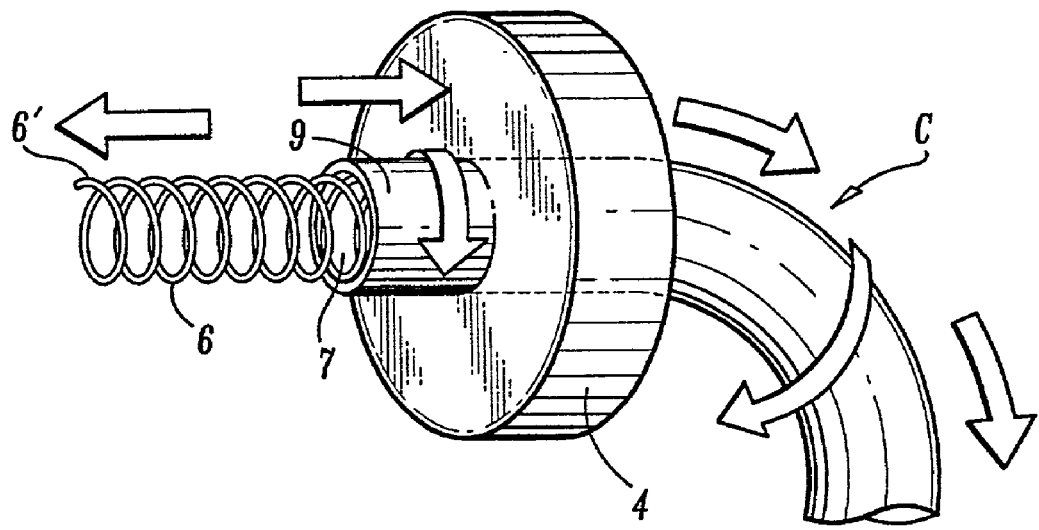
FIG. 5b is a detail, as in FIG. 5a, but showing the disconnection movements of the applicator end of the semi-flexible cable.

LIST OF THE MAIN REFERENCES (a) vascular channel for application
(b) prosthetic body
(c) semi-flexible cables
(1) cylindrical walls of prosthetic body (b)
(1') prosthetic passage delimited by cylindrical walls (1)
(2) internal surfaces of cylindrical walls (I)
(3) external surfaces of cylindrical walls (1)
(4) connector in form of small disk
(4') base of connector (4)
(4") mouth of connector (4)
(5) vascular walls of vascular channel (a)
(6) spiral sutures
(6') sharpened penetrating end of spiral suture (6)
(7) anchoring end of spiral suture (6)
(8) long body of semi-flexible cable (6)
(9) rotary applicator end, disconnectable from cable (b)
(9') external rotary control end of cable (b).

DESCRIPTION OF THE PREFERRED EMBODIMENTS

For the purposes specific, this endovascular prosthesis with suture holder is of the type that, since it can be introduced endoluminally into vascular channel (a) for the application, comprises prosthetic body (b) with cylindrical walls (1) and open bases, the is expandable radially up to the limit at which its external surfaces (3) comb into contact with damaged vascular walls (5) of the above-cited vascular channel (a), with internal surfaces (2) of said body (b) forming prosthetic circulatory passage (1'); said endovascular prosthesis is characterized in that it comprises:

a) a number of connectors (4) that, distributed such that they encircle the cylindrical walls (I) of prosthetic body (b), are attached to internal surfaces (2) of said cylindrical walls (1);
 b) in each connector (4), rotary end (9), which is disconnectable from respective semi-flexible cable (c) for applying sutures (6), which cable (c) extends beyond said prosthetic passage (1'), ending in an external rotary control end (9'); and
 c) passing through each connector (4) and cylindrical wall (1) adjacent to said prosthetic body (b), respective spiral suture (6), the anchoring ends (7) of which are inserted in said rotary end (9) of its respective semi-flexible cable (b).

This invention consists of an endovascular prosthesis with suture bolder that, in general) terms, comprises prosthetic body (b) on internal surfaces (2) of which a number of connectors (4) are distributed and attached that, on the one hand, connect respective semi-flexible cables (b) ending in external rotary control ends (9'), while, on the other hand, they are passed through by respective spiral sutures (6) controlled by said semi-flexible cables (b).

More particularly, the endovascular prosthesis consists of prosthetic body (b) with cylindrical walls (1) and open bases that can be introduced into vascular channel (a) for the application until it reaches its position with regard to the damaged vascular walls (5). It is a prosthetic body (5) that can be expanded radially up to the limit at which its cylindrical walls (1) contact above-cited vascular walls (5).

In various methods of embodiment, prosthetic body (b) can be composed of a thermo-expandable material or a material expandable by means on an inflatable balloon or similar device.

Cylindrical walls (1) of prosthetic body (b) are delimited by external (3) and internal (2) surfaces. It is precisely on the internal walls (2) that a number of connectors (4) are attached that, in the method of embodiment described, consist of parts in the shape of small disks, the mouth (4") of which is placed against internal surface (2), while its base (4') remains exposed inside prosthetic passage (1') made up of cylindrical walls (1). These connectors (4) are distributed inside cylindrical walls (1), lining them in a circular manner.

At each connector (4), there terminates respective semi-flexible cable (c) for application of sutures (6), for which reason, for each connector (4) available, the prosthesis has a semi-flexible cable (c). This latter (c) consists of long body (8) with applicator end (9) that can be disconnected from connector (4) to which it is connected. Starting from this disconnectable applicator end (9), semi-flexible cable (c) extends beyond the prosthetic passage (1') until it projects from vascular channel (a), ending in an external control end (9') which can be connected to a rotary device.

Moreover, each connector (4) is passed through by respective spiral suture (6) provided with sharpened penetrating end (6') and, at the opposite end, with anchoring end (7). These spiral sutures (6) pass through connectors (4) and prosthetic walls (1) equipped at two alternative end positions: one for prosthetic positioning, at which anchoring ends (7) are inserted into applicator ends (9) of their respective semi-flexible cables (c); and the other position for placement of the prosthesis, in which sharpened ends (6') of said spirals (6) protrude through prosthetic walls (1) and pass through vascular walls (5) for the application.

In this second, prosthetic-placement position, bases (4') of connectors (4) constitute a penetration stop for anchoring ends (7) of spiral sutures (6).

The unit functions in the following manner:

By means of any suitable introductory device, the endovascular prosthesis is introduced through vascular channel (a) for the application until it reaches its position with regard to damaged vascular walls (5).

Under these conditions, prosthetic body (b) is contracted and spiral sutures (6) passed through connectors (4) and cylindrical walls (1) of prosthetic body (b), although without projecting externally therefrom further than its external surface (3).

Once prosthetic body (b) is expanded, its external surfaces (3) are in contact with vascular walls (1). With this arrangement, the rotary actuation of semi-flexible cables (c) permits penetration ends (6') of spirals (6) to pass through vascular walls (5). This penetration continues until anchoring ends (7) of above-cited spirals (6) stop against bases (4') of respective connectors (4). In this manner, a firm union is created between vascular channel (a) and prosthetic body (b).

It is indubitable that, once this device is used in practice, changes can be made in certain design and form details without escaping from the fundamental principles substantiated clearly in the following Claims.

I claim:

1. An endovascular prosthesis system comprising
 a prosthesis body sized and configured for introduction into a blood vessel lumen and including a wall defining an interior passage for blood,
 means for radially expanding the wall of the prosthetic body into contact with the blood vessel lumen,
 a plurality of connectors attached to the wall in a circumferentially spaced distribution, and
 a tissue piercing spiral suture carried by each of the connectors, each tissue piercing spiral suture including a sharpened penetrating end that pierces tissue in response to rotation of the tissue piercing spiral suture,
 a plurality of semi-flexible cables, each semi-flexible cable including a distal end releasably connected to one of the tissue piercing spiral sutures carried by one of the connectors and a proximal end that extends to a remote location outside the blood vessel lumen, and
 an external rotary driver sized and configured to be coupled to the proximal end of each semi-flexible cable to rotate the semi-flexible cable and thereby rotate the tissue piercing spiral suture carried by the respective connector to pierce tissue and advance through the connector into tissue in the blood vessel lumen,
 each connector further including a base comprising a tissue penetration stop for the tissue piercing spiral suture.

2. A prosthesis system according to claim 1
 wherein the means for radially expanding the wall of the prosthesis body into contact with tissue in the blood vessel lumen includes thermal expansion.

3. A prosthesis system according to claim 1
 wherein the means for radially expanding the wall of the prosthesis body into contact with tissue in the blood vessel lumen includes an expandable body expandable within the prosthesis body.

* * * * *

UNITED STATES PATENT AND TRADEMARK OFFICE
CERTIFICATE OF CORRECTION

PATENT NO.          : 7,591,842 B2                                        Page 1 of 1
APPLICATION NO.     : 09/935893
DATED               : September 22, 2009
INVENTOR(S)         : Juan C. Parodi It is certified that error appears in the above-identified patent and that said Letters Patent is hereby corrected as shown below:

Title Page under Item (22) insert
--(30) Foreign Priority
    Argentina Application No. P19980101144, filed March 13, 1998--

Signed and Sealed this

Twenty-second Day of December, 2009

David J. Kappos
*Director of the United States Patent and Trademark Office*